US005791342A

United States Patent [19]
Woodard

[11] Patent Number: 5,791,342
[45] Date of Patent: Aug. 11, 1998

[54] MEDICAL DATA TRANSMISSION SYSTEM

[75] Inventor: Larry L. Woodard, Colma, Calif.

[73] Assignee: Telediagnostics Systems, Inc., San Francisco, Calif.

[21] Appl. No.: 707,327

[22] Filed: Sep. 3, 1996

[51] Int. Cl.$^6$ .................................................. A61B 5/04
[52] U.S. Cl. .......................... 128/630; 128/700; 128/731; 128/904
[58] Field of Search ..................... 128/630, 653.1, 128/696, 700, 710, 731, 903, 904; 364/413.05, 413.06

[56] References Cited

U.S. PATENT DOCUMENTS

| | | | |
|---|---|---|---|
| 4,449,536 | 5/1984 | Weaver | 128/696 |
| 5,012,411 | 4/1991 | Policastro et al. | 128/710 |
| 5,255,186 | 10/1993 | Steinhaus | 128/700 X |
| 5,263,486 | 11/1993 | Jeffreys | 364/413.06 |
| 5,365,428 | 11/1994 | de Pinto et al. | 364/413.06 |
| 5,377,258 | 12/1994 | Bro | 379/93 |
| 5,437,278 | 8/1995 | Wilk | 128/653.1 |
| 5,534,851 | 7/1996 | Russek | 340/573 |

OTHER PUBLICATIONS

Womble, M.E. et al "Data Compression for Storing and Transmitting ECG's/VCG's", Proc. of the IEEE vol. 65 No. 5 May 1977.

T. Kientzle, "The Working Man's Guide To Serial Protocols," (The Coriolis Group 1995).

Works-in-Progress Abstract #E139, "Digital Telephonic EEG Transmission and Receiving System," p. 7, American Electroencephalographic Society Annual Meeting, Washington, DC (Sep. 7-12, 1995).

Works-in-Progress Abstract #E139, "Digital Telephonic EEG Transmission and Receiving System," *J. Clin. Neurophysiol.*, 13(4):353 (1996).

*Primary Examiner*—Francis Jaworski
*Attorney, Agent, or Firm*—Flehr, Hohbach, Test, Albritton & Herbert, LLP

[57] ABSTRACT

A medical data transmission system which, at the transmitting end, is comprised of a detection means for the detection of various physiological parameters of a patient and a pre-transmission processing means for digitizing and processing the detected analog signals. The optimal digitized data is then transmitted via a data transmission linkage and a suitable transmission medium such as a conventional telephone line to a post-transmission processing means at the receiving end. The post-transmission processing means buffers and processes the transmitted digitized data, which is then reconverted to create an accurate analog reconstruction of the physiological signals as detected at the patient location.

20 Claims, 4 Drawing Sheets

MEDICAL DATA TRANSMISSION SYSTEM

FIELD OF THE INVENTION

This invention relates to the field of data transmissions. More particularly, this invention relates to the field of medical data transmissions over a limited bandwidth transmission medium such as voice-grade telephone lines.

BACKGROUND OF THE INVENTION

Medical data in the form of direct measurements of various biological or physiological parameters plays a crucial role in the proper diagnosis and treatment of many medical conditions. In particular, physiological data representing the electrical potential at different points on a patient's body (i.e., EEG, EKG, EMG, and EOG signals) can provide both emergency and medical personnel with invaluable information regarding a patient's contemporaneous cardiac and neurological function, and can be advantageously used both in emergency life-threatening situations as well as in pre- and post-treatment evaluation of an existing medical condition.

Within the past decade, there have been great advances in computer-based diagnostics for this type of medical data. For example, brain-mapping and quantitative EEG analysis systems have recently been developed which provide additional valuable clinical information, to aid doctors and researchers in EEG-based neurodiagnostics. In order to increase the efficient use of these computer systems, which can be prohibitively expensive to acquire and maintain, conventional telephone lines have been proposed as possible mediums for the transmission of medical data from remote locations. This would allow smaller hospitals, clinics and individual doctor's offices to have direct access to these computer systems and the information they provide.

However, these improved analytical computer systems also have substantially increased data input requirements, which are well beyond the range of conventional data transmission systems, both analog and digital. For example, the EEG-based diagnostic computer systems described above typically require a minimum input of sixteen simultaneous channels of EEG data, and existing data transmission systems are only capable of transmitting ten channels of data at a time using FM transmission frequencies, and typically less than five channels over conventional telephone lines. Thus, prior art data transmission systems are severely limited in their ability to provide for the real-time transmission of an adequate number of simultaneous channels of medical data, particularly over a limited-bandwidth transmission medium such as voice-grade telephone lines.

Moreover, another problem persists in the art with respect to the accurate reconstruction of digitally sampled (or "digitized") medical data after transmission to a receiving location. In digital data transmission systems the analog signal produced by an EEG measuring device is initially converted into a digital signal at the transmitting end, then reconstructed back into an analog signal at the receiving end for display, recording and analysis of the data. Unfortunately, existing transmission systems do not provide adequate data reconstruction fidelity of the digitized waveform data, since clinically-significant waveforms in the initial analog signal can be lost through conventional fixed sampling techniques, and artifacts of the digital-to-analog conversion process at the receiving end can be misinterpreted by a quantitative EEG analysis system as high frequency data components.

Accordingly, there is a substantial need in the art for a data transmission system which is capable of transmitting a large number of channels of digitized medical data simultaneously and in real-time over a limited-bandwidth transmission medium such as a voice-grade telephone line. Such a system should also provide a method for the pre- and post-processing of the digitized waveform data to provide for the highest achievable data reproduction fidelity at the receiving end, so that the reconstructed analog signal will provide an accurate representation of the transmitted physiologic parameters of the patient.

SUMMARY OF THE INVENTION

Accordingly, it is an object of the present invention to remedy the disadvantages encountered in prior art medical data transmission systems, through the provision of a data transmission system capable of transmitting a large number of channels of data simultaneously across a limited bandwidth transmission medium.

In one embodiment, the medical data transmission system of the present invention comprises: (a) a detection means for detecting at least one physiological parameter from a patient; (b) a pre-transmission processing means for digitally sampling and transmitting the detected analog signals, said pre-transmission processing means coupled to said detection means; (c) a data transmission linkage which transmits more than ten channels of the digitized data samples to a receiving location, said data transmission linkage coupled to said pre-transmission processing means; and (d) a post-transmission processing means coupled to said data transmission linkage at said receiving location for converting said digitized data samples and accurately reconstructing said analog signal. In a particularly preferred embodiment, said physiological parameter is selected from the group comprising: EEG signals, EKG signals, EMG signals, EOG signals, respiration signals, and oximetry signals measuring oxygen saturation. In another embodiment, said detection means is capable of detecting more than ten channels of physiological parameters from a patient.

In one embodiment, said pre-transmission processing means incorporates an analog-to-digital converter. In a preferred embodiment, said pre-transmission processing means digitally samples said detected analog signals at a rate which is at least ten times greater than the actual data transmission rate, and selects optimal digitized data samples prior to transmission. In a particularly preferred embodiment, said pre-transmission processing means selects optimal digitized data samples prior to transmission by: (a) calculating the minimum, maximum and average values for a set of said digitized data samples; (b) if the difference between the minimum and maximum values is less than or equal to 15% of the full scale range of said analog-to-digital converter, selecting and transmitting the average value for said set of digitized data sample; (c) if the difference between the minimum and maximum values is greater than 15% of the full scale range of said analog-to-digital converter, and the average value for said set of digitized data samples is less than the average value for the preceding set of data samples, selecting and transmitting the minimum value for said set of digitized data samples; and (d) if the difference between the minimum and maximum values is greater than 15% of the full scale range of said analog-to-digital converter, and the average value for said set of digitized data samples is greater than the average value for the preceding set of data samples, selecting and transmitting the maximum value for said set of digitized data samples.

In one embodiment, said data transmission linkage comprises a transmitting computer coupled with a receiving computer over a transmission medium via a pair of modems. In a particularly preferred embodiment, said transmission medium comprises a voice-grade telephone line.

In one embodiment, said post-transmission processing means buffers said digitized data upon receipt to ensure continuous analog signal reconstruction. In a further embodiment, said post-transmission processing means performs a smoothing method on said digitized data. In a particularly preferred embodiment, said smoothing method comprises the insertion of intervening data points into said digitized data. In another embodiment, said post-transmission processing means comprises a digital-to-analog converter for reconstructing said detected analog signal corresponding to said physiological parameter of said patient. In a still further embodiment, said post-transmission processing means further comprises at least one analog low-pass filter.

The present invention also contemplates a method for the transmission of medical data through a transmission medium. In one embodiment, this method comprises (a) detecting at least one physiological parameter from a patient; (b) pre-processing the analog signals corresponding to said detected physiological parameter into digitized data samples; (c) transmitting said digitized data samples across more than ten transmission channels to a receiving location; and (d) post-processing said digitized data samples at said receiving location to accurately reconstruct said analog signals. In a preferred embodiment of the method of the present invention, said physiological parameter is selected from the group comprising: EEG signals, EKG signals, EMG signals, EOG signals, respiration signals, and oximetry signals.

In a preferred embodiment, said pre-processing step comprises digitally sampling said analog signals at a rate which is at least ten times greater than the actual data transmission rate, and performing a data reduction method on the digitized data samples. In a particularly preferred embodiment, said data reduction method comprises: (a) calculating the minimum, maximum and average values for a set of said digitized data samples; (b) if the difference between the minimum and maximum values is less than 15% of the full scale range of the analog-to-digital converter, selecting and transmitting the average value for said set of digitized data samples; (c) if the difference between the minimum and maximum values is greater than 15% of the full scale range of the analog-to-digital converter, and the average value for said set of digitized data samples is less than the average value for the preceding set of data samples, selecting and transmitting the minimum value for said set of digitized data samples; and (d) if the difference between the minimum and maximum values is greater than 15% of the full scale range of the analog-to-digital converter, and the average value for said set of digitized data samples is greater than the average value for the preceding set of data samples, selecting and transmitting the maximum value for said set of digitized data samples.

In another preferred embodiment of the present invention, said post-processing step comprises performing a smoothing method on said digitized data samples prior to converting said digitized data samples back into an analog signal. In a particularly preferred embodiment, said smoothing method comprises the insertion of intervening data points into said digitized data. In yet another preferred embodiment, said post-processing step further comprises buffering said digitized data for a predetermined length of time prior to performing said smoothing method on said digitized data samples.

An alternative embodiment of the medical data transmission system of the present invention comprises: (a) a detection means for detecting at least one physiological parameter from a patient; (b) a pre-transmission processing means for digitally sampling said detected analog signals and selecting optimal digitized data samples for transmission, said pre-transmission processing means coupled to said detection means; (c) a data transmission linkage comprising a transmitting computer coupled with a receiving computer over a telephone line via two modems, which transmits more than ten channels of said digitized data samples to a receiving location, said data transmission linkage coupled to said pre-transmission processing means; and (d) a post-transmission processing means coupled to said data transmission linkage at said receiving location for buffering said digitized data samples and performing a smoothing method on said digitized data samples prior to reconstructing said analog signal from said digitized data samples.

Other and further objects, features, advantages and embodiments of the present invention will become apparent to one skilled in the art from reading the detailed description of the invention together with the drawings.

DESCRIPTION OF THE INVENTION

The methods and apparatus of the present invention solve the problems present in the prior art by providing a medical data transmission system which, at the transmitting end, is comprised of a detection means (i.e. a physiological amplifier) for the detection of various physiological parameters such as EEG or EKG signals. This detection means is interfaced with a pre-transmission processing means for digitizing and processing the detected analog signals. In one of the methods of the present invention, the desired physiological data is collected and digitally sampled at a rate which is much higher than the rate which will actually be transmitted, and a data reduction method is applied to select optimal digitized data samples for transmission. This optimized and digitized data is then transmitted to the receiving end via a transmission linkage, comprising a transmitting computer and a first modem, which can be advantageously connected to a conventional voice-grade telephone line or any other suitable transmission medium.

The transmission linkage of the present invention is further comprised, at the receiving end, of a second modem and a receiving computer connected to the voice-grade telephone line or other transmission medium so as to receive the data from the transmitting end. The received digital data is supplied via the receiving computer to the post-transmission processing means for the purposes of buffering, and for implementing a smoothing method to help eliminate the "steps" in the digital data through the insertion of intervening data points. Said post-transmission processing means further operates to control a digital-to-analog conversion system to create a precise analog reconstruction of the physiological signals as detected at the patient location.

As described more fully below, the pre- and post-transmission data processing methods contemplated by the present invention enable the transmission and accurate reconstruction of EEG waveforms (in analog form) at the receiving end across a significantly larger number of transmission channels than possible in the prior art. These processing steps also substantially eliminate the likelihood that clinically-significant waveforms will be lost during the analog-to-digital conversion at the transmitting end, and furthermore substantially reduce the artifacts created by the digital-to-analog conversion at the receiving end.

DETAILED DESCRIPTION OF THE PREFERRED EMBODIMENTS

The following description serves to illustrate certain preferred embodiments and other aspects of the present invention, and is not to be construed as limiting the scope thereof.

Figure 1:
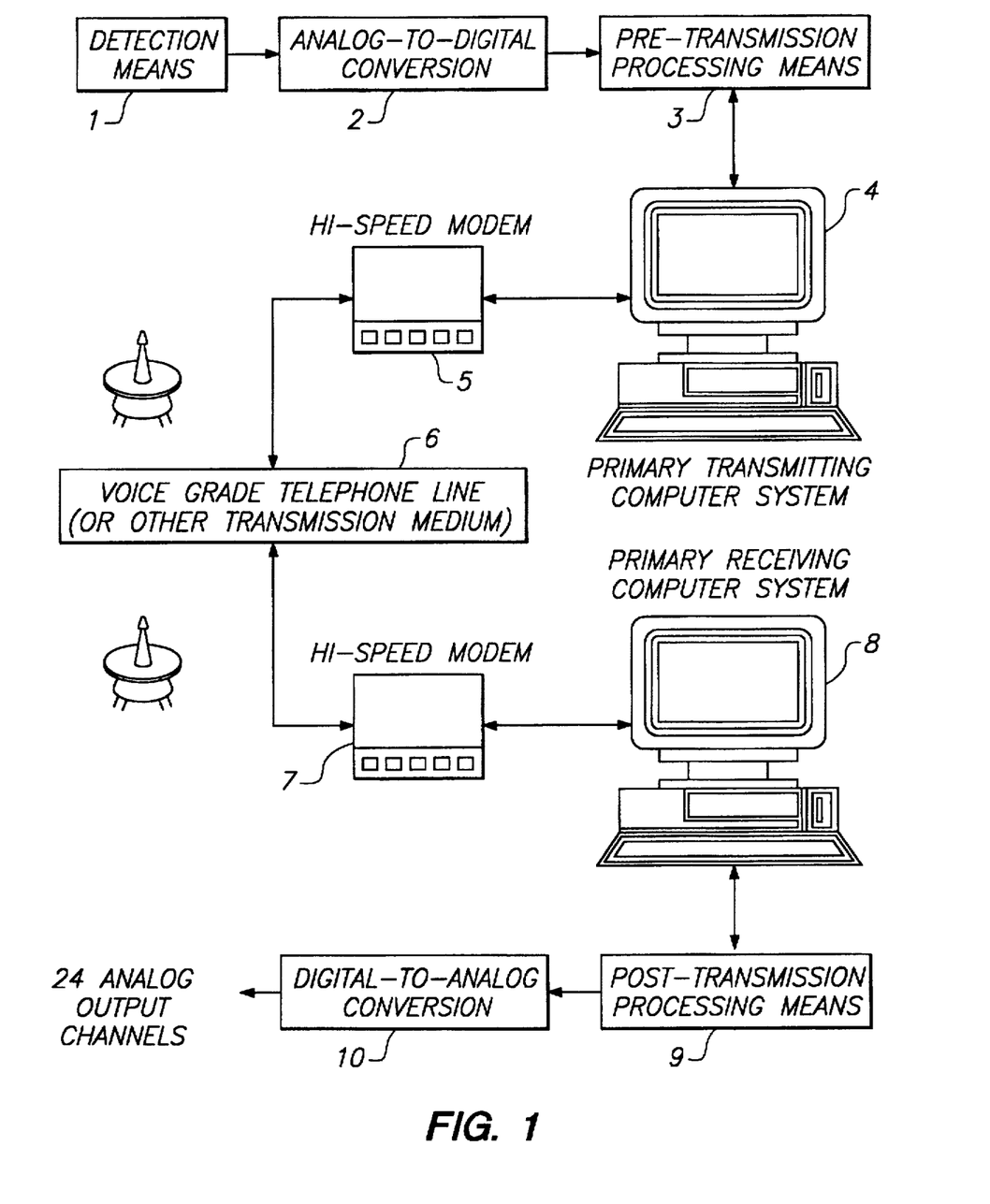
FIG. 1 illustrates a block diagram of one embodiment of a medical data transmission system in accordance with the present invention.

FIG. 1 provides a block diagram of a preferred embodiment of the medical data transmission system of the present invention. In this embodiment a detection means comprising a physiological amplifier 1 is provided for the detection of physiological parameters from a patient. For the purposes of the present invention the amplifier must be capable of detecting a large number of channels (i.e. more than ten). In a particularly preferred embodiment, the amplifier of the present invention is designed for the detection of 21 channels of EEG, 2 channels of EOG, and 1 channel of EKG, for a total of 24 channels. However, other numbers and types of AC or DC transmission channels and physiological parameters, such as EEG, EKG, EOG, EMG, respiration and oxygen saturation, may be used as required for each particular application.

As noted previously, one goal of the present invention is to be able to reproduce (in analog form) accurate EEG waveforms at the receiving location with an upper frequency in the range of approximately 40 to 45 hertz ("Hz"), across a significantly larger number of transmission channels. In a preferred embodiment, there are more than ten transmission channels. In a particularly preferred embodiment, there are 24 transmission channels. Using conventional criteria, the minimum sample rate for an accurate analog reconstruction of the signal is typically on the order of eight times the highest frequency of interest. According to accepted criteria, therefore, to transmit a 40 Hz signal would require a sample rate of approximately 320 samples per second, which would in turn require a bandwidth of approximately 7680 samples per second for the 24 transmission channels contemplated above.

Unfortunately, a conventional voice-grade telephone line in conjunction with a 28.8K baud modem provides a maximum data transmission rate only on the order of approximately 3000 samples per second (because this is a maximum, it is typically somewhat less). Thus, a conventional phone line combined with a high speed 28.8K baud modem provides less than one-half the required bandwidth for a visually-accurate analog reconstruction of 24 channels of EEG data. In order to compensate for this fact, the present invention incorporates several pre- and post-transmission data processing methods to provide an enhanced signal reproduction capability with the limited data transmission rate available on conventional voice-grade telephone lines.

The analog output signals from the amplifier 1 are first fed through an analog-to-digital (A/D) converter 2 for converting the signals to a digital format. The A/D converter 2 is an integral part of the pre-transmission processing means 3 which collects, buffers, and pre-processes the digital data to be transmitted. It is contemplated that the pre-transmission processing means will be capable of digitizing and processing the raw physiological data at a rate which is at least ten times greater than the actual data transmission rate. This over-sampled data is then reduced to the actual data transmission rate through the application of the data reduction method of the present invention, in order to accomodate the desired number of transmission channels.

The data reduction method of the present invention also reduces the likelihood that clinically-significant waveforms will be lost during the conversion and transmission of the digitized data. The nature of this aspect of the pre-processing step is illustrated by the example shown in FIGS. 2A–C.

Figure 2A:
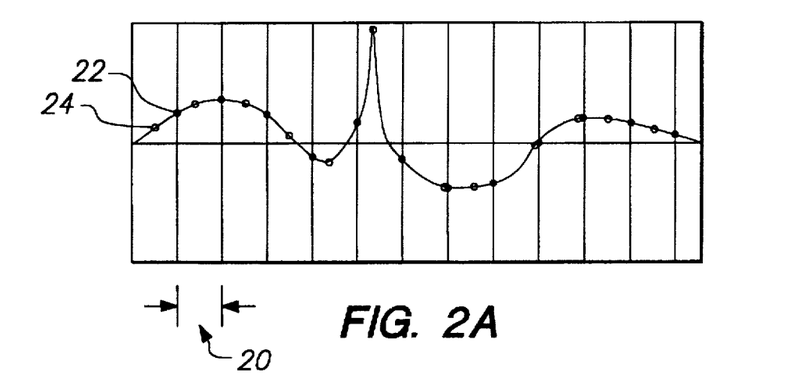
FIGS. 2A–C illustrate data processing of the pre-transmission waveform.
Figure 2B:
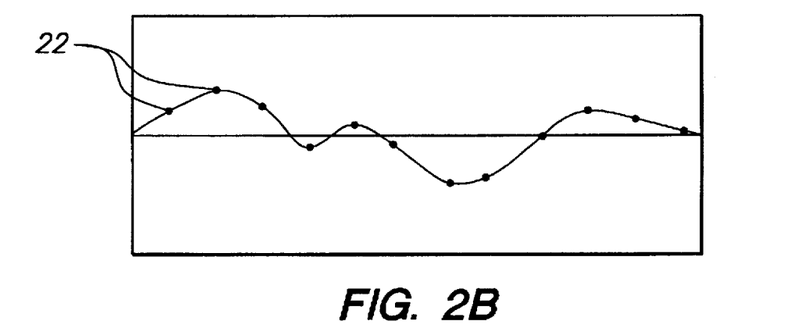

Specifically, within the field of EEG, there are clinically-significant waveform components which are commonly referred to as "spikes." These EEG spikes are characterized by having a very transient and short time duration along with a high amplitude. An example of a waveform containing a transient spike component is shown in FIG. 2A. Consider the case where this waveform has been digitized at a sample rate of 100 samples per second. The sample interval 20 in FIG. 2A would therefore represent 10 milli-seconds. The transient peak which occurs near the middle of this waveform has a time period which is just less than the sample interval. When the waveform shown in FIG. 2A is digitized at a fixed sample rate of 100 samples per second, the fixed space data samples 22 represented by the solid circles will be collected. When the waveform is then reconstructed using these data points the result will be as shown in FIG. 2B. As can be seen, the transient spike component has been lost.

The present invention contemplates that the data is sampled at a much higher rate than will actually be transmitted. In this case, instead of a single sample being collected during each sample interval, a total of 10 samples are collected which represents a digitizing rate of 1000 samples per second. This over-sampled data is stored within the memory buffer of the pre-transmission processing means 3, and a data reduction method is applied to the stored data samples to reduce them to the desired equivalent sample rate and select the optimal data sample for transmission.

Figure 3:
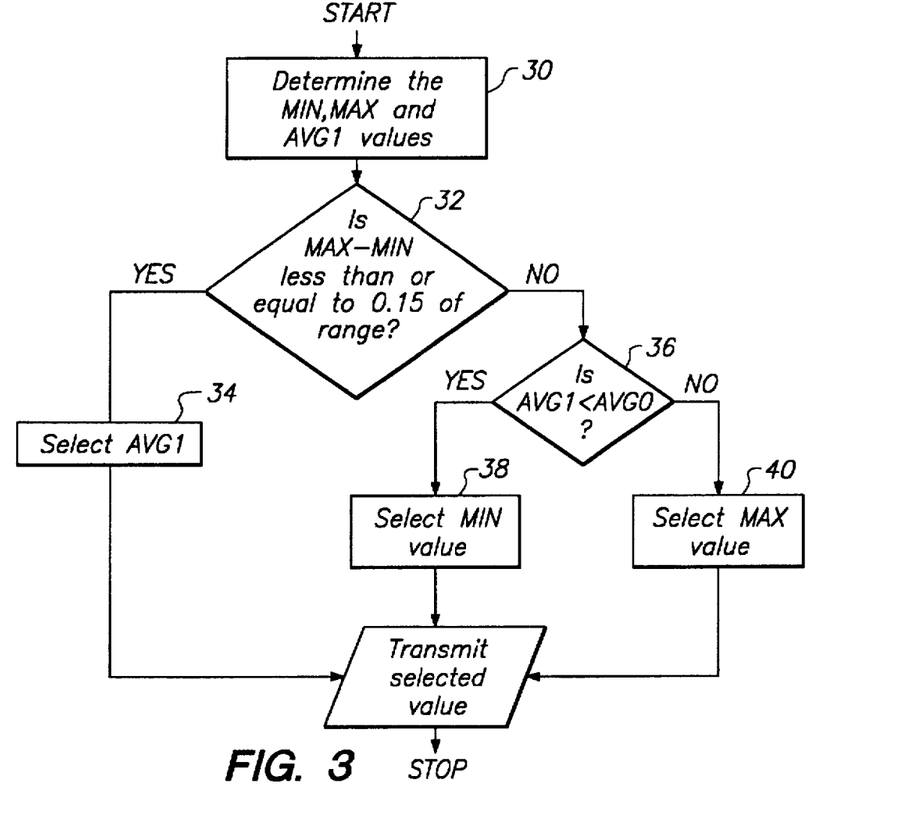
FIG. 3 is a flow diagram of one embodiment of the data reduction method of the present invention.

A preferred embodiment of the data reduction method of the present invention operates as shown in the flow chart in FIG. 3. As illustrated in FIG. 3, the minimum (MIN), maximum (MAX), and average values (AVG1) are calculated for a predetermined group of data samples 30. In this example, the group comprises ten data samples. In the next step, the difference between the minimum and maximum values is compared with the full scale range of the A/D converter 32. If the difference is less than or equal to 15% of the full scale range of the A/D converter, then the average value (AVG1) is selected from that group 34. If the difference between the minimum and maximum values is greater than 15% of the full scale range, then the average value from this group (AVG1) is compared with the average value from the preceding group (AVG0) 36. If the average value from this group is less than the average value from the preceding group, then the minimum value is selected 38. If the average value (AVG1) is greater than the average value from the preceding group (AVG0), then the maximum value is selected 40.

Figure 2C:
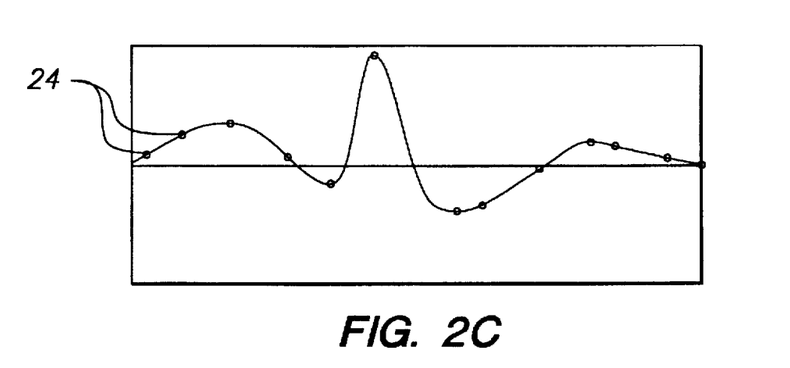

When this data reduction method is applied to the over-sampled data stored within the buffer of the pre-transmission processing means 3, the optimal data samples 24 as illustrated by the open circles in FIG. 2A will be selected for each sample interval. When the waveform is reconstructed using these optimal data samples the results will be as shown in FIG. 2C. As can be seen, in this case the occurrence of the transient spike component of the original waveform has now been preserved. Of course, the particular number of data samples, and the thresholds and methods used for processing, are merely representative of one preferred embodiment of this invention. It is contemplated that other sample numbers and processing methods may be applied for the purpose of data reduction and heuristic feature retention, and still be within the spirit of this invention.

The reduced and processed data is then supplied to the data transmission linkage, which in a preferred embodiment comprises a transmitting computer 4 coupled with a receiving computer 8 over a suitable transmission medium via a pair of modems 5 and 7. In a particularly preferred embodiment, the data transmission linkage comprises a pair of IBM-compatible computers and hi-speed (i.e. 28.8K baud or higher) modems connected via a conventional voice-grade telephone line 6. Of course, it is also contemplated that the methods and apparatus of the present invention can be easily and advantageously interfaced with other forms of data transmission, such as ISDN lines, T1 lines, Internet Connections, or Local Area Network systems. Alternative computer and various modem arrangements can easily be incorporated into the data transmission linkage of the present invention to accomodate these alternative transmission mediums.

Within the preferred embodiment of the current invention the digitized data transmitted over the telephone line 6 is organized into one-second packets of data samples. Numerous protocols exist for the transmission of data and are well known in the art. See, e.g., T. Kientzle, "The Working Programmer's Guide To Serial Protocols" (The Coriolis Group 1995). The medical data transmission system of the present invention is not limited to any specific transmission protocol, other than the requirement that the system have the capability to dynamically adjust the data sample rate according to the bandwidth currently available through the transmission link. Thus, the system must be able to detect the amount of data collected in the buffer of the pre-transmission processing means, and alternate between at least two distinct data sample rates in order to adjust for the amount of digitized data actually being transmitted out of the buffer and through the link.

For example, in the preferred embodiment described herein, the transmission protocol utilized by the data transmission system has the ability to switch between a fast sample rate of 128 samples per second per channel, and a slow sample rate of 100 samples per second per channel. In this embodiment it is contemplated that the transmission will begin at the fast sample rate. If the system detects that the amount of buffered data is increasing, indicating that the transmission link is not keeping up with the digitizing rate, then the sample rate is switched to the slow rate. When the data remaining in the buffer has decreased to a given threshold, for example 2 seconds, the sample rate is again switched to the fast rate. It is further contemplated that each one-second packet of data transmitted through the system is encoded at the start of the packet with an indication of the sample rate for that packet, as is well known in the art.

The digitized data received by the receiving computer 8 is then supplied to the post-transmission processing means 9. In the preferred embodiment described herein the post-transmission processing means 9 performs three primary functions: (1) the transmitted data is buffered to allow for a continuous analog signal reconstruction despite fluctuations and pauses which may occur in the transmission link; (2) a smoothing method is performed on the buffered data to insert additional data points, which results in a smoother analog signal reconstruction after the digital-to-analog conversion process; and (3) data and timing signals are supplied to a digital-to-analog (D/A) converter 10 to produce an analog reconstruction of the physiological signals which were detected from the patient at the transmitting location.

With respect to the first feature identified above, the transmitted data is collected at the receiving end and buffered within the memory of the post-transmission processing means 9. In the preferred embodiment described herein, this buffer holds five seconds worth of transmitted data, which allows for a continuous analog reconstruction of the transmitted data despite fluctuations and pauses during transmission. However, the specific size of this buffer is not limited in the present invention, it is only required that the final output from the system be reasonably close to real-time, and therefore for practical purposes the content of the buffer should not exceed approximately fifteen to twenty seconds worth of transmitted data.

Figures 4A, 4B:
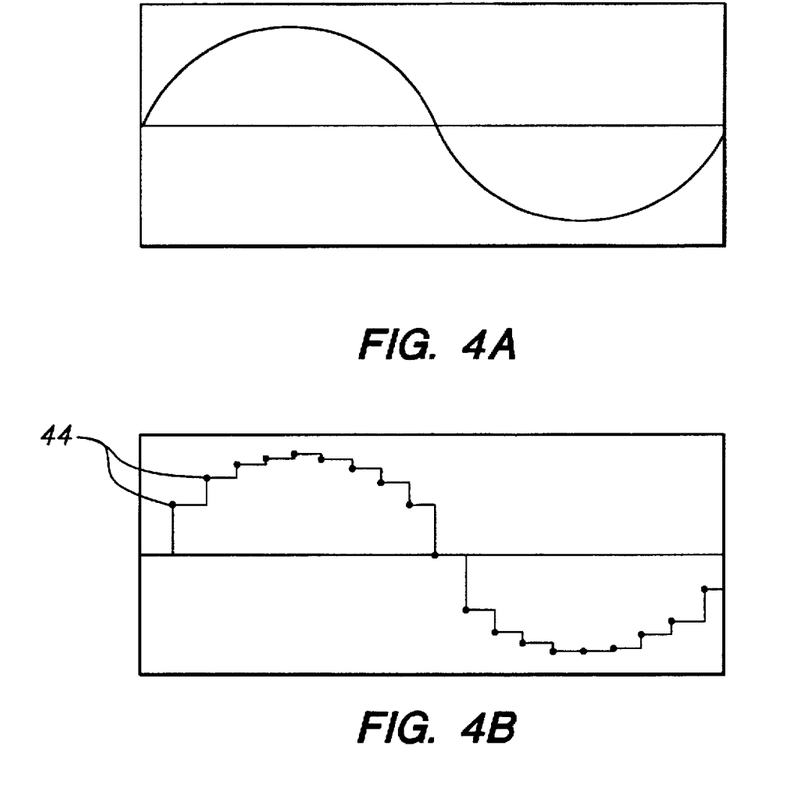
FIGS. 4A–C illustrate data processing of the post-transmission waveform.
Figure 4C:
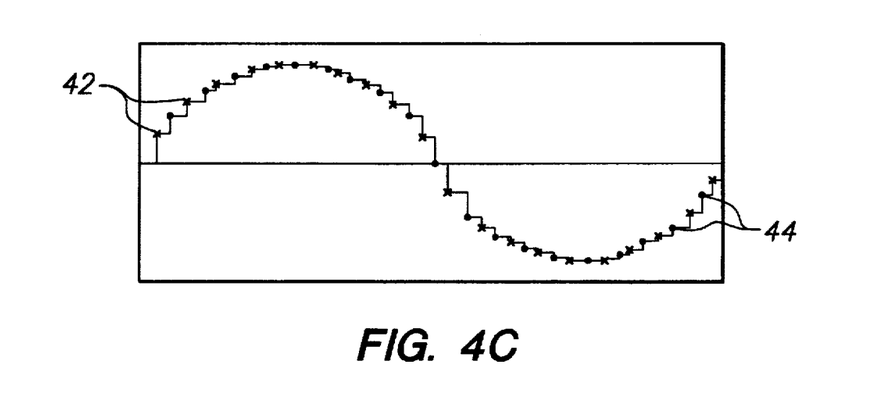

With respect to the second feature of the post-transmission processing means 9, the operation of a preferred embodiment of the data smoothing algorithm is illustrated in FIGS. 4A–C. When a digitized waveform is converted back to analog form, the normal result is an analog waveform composed of digital "steps" as shown in FIG. 4B. This digital "steppiness" is characteristic of digital-to-analog converter outputs and creates problems when the resulting signal is intended to interface with a quantitative EEG analysis system. The EEG analysis system will interpret this signal as containing high frequency data components, which are actually artifacts of the digital-to-analog conversion process. This phenomenon is minimized by the post-transmission data processing method of the present invention.

Figure 5:
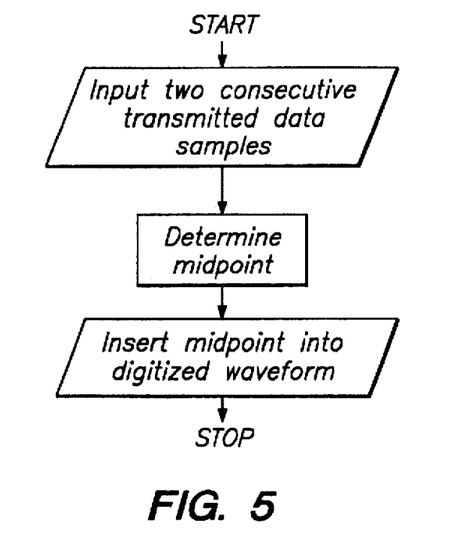
FIG. 5 is a flow diagram of one embodiment of the smoothing method of the present invention.

With this method an additional data point 42 is inserted between each pair of transmitted digital samples 44. This point 42 is so calculated as to represent the mid-point between the samples 44. The result is a reduction by a factor of two in the size of the digital steps in the reconstructed analog waveform as is illustrated by FIG. 4C. A flow diagram illustrating this preferred embodiment of the smoothing method of the present invention is provided in FIG. 5. Of course, alternative post-transmission processing techniques can also be beneficially employed to help eliminate these digital steps, and are considered to be within the spirit and scope of the present invention.

Finally, the digitized data is interfaced to the digitial-to-analog converter 10 in order to recreate the analog waveform of the patient's physiological parameters. It is further contemplated that the small amount of remaining digital steppiness in the output is further removed with analog low pass filters (not shown). Thus, the final output of the data transmission system of the present invention is an accurate analog reconstruction of the physiological parameters which were detected from the patient at the transmitting end. It is contemplated that this analog reconstruction can then be universally interfaced with other existing systems for the display, recording and analysis of the transmitted data as if the patient were present at the receiving location.

It should again be noted that the present invention has been described in terms of a preferred embodiment. One skilled in the art will recognize that it would be possible to substitute for various elements of the present invention and to modify the transmission scheme and the placement of the components in a variety of ways. For example, in the preferred embodiments described above the pre- and post-transmission processing means are independent systems with their own CPU, memory, and software, which operate independently of the primary transmitting and receiving computers. In this embodiment these processing systems are implemented as single printed circuit boards inserted into the primary transmitting and receiving computers, which communicate with these computers via the ISA expansion bus. However, it is well within the contemplation of the present invention that with faster and more powerful computers (including non-IBM-compatible computers) all processing at the transmission and/or receiving sites could be performed within a single integrated system.

Moreover, it is also contemplated that the medical data transmission system of the present invention can be advantageously utilized in a wide variety of applications, and can easily be adapted to interface with any number of physiological measuring devices, including, for example, pulmonary function apparatus, doppler study apparatus, MRI apparatus, CAT scanner, X-ray machine, ultrasonagraphy apparatus, electronic thermometer or blood pressure gauge, and/or pressure measurement device, as well as the EEG, EKG, EMG, EOG, respiration and/or oximetry machines discussed above. The methods and apparatus of the present invention may also find advantageous use in transmitting other types and forms of non-medical data. While the preferred embodiments have been described in detail and shown in the accompanying drawings, it will be evident that various further modifications are possible without departing from the scope of the invention as set forth in the following claims.

I claim:

1. A medical data transmission system, comprising:
   (a) a detection means for detecting at least one physiological parameter from a patient;
   (b) a pre-transmission processing means for digitally sampling and transmitting the detected analog signals in real-time, said pre-transmission processing means coupled to said detection means;
   (c) a data transmission linkage which simultaneously transmits more than ten channels of the digitized data samples to a receiving location, said data transmission linkage coupled to said pre-transmission processing means; and
   (d) a post-transmission processing means coupled to said data transmission linkage at said receiving location for converting said digitized data samples and accurately reconstructing said analog signal.

2. The medical data transmission system of claim 1, wherein said physiological parameter is selected from the group comprising: EEG signals, EKG signals, EMG signals, EOG signals, respiration signals, and oximetry signals.

3. The medical data transmission system of claim 1, wherein said detection means is capable of detecting more than twelve channels of physiological parameters from a patient.

4. The medical data transmission system of claim 1, wherein said pre-transmission processing means incorporates an analog-to-digital converter.

5. The medical data transmission system of claim 1, wherein said pre-transmission processing means digitally samples said detected analog signals at a rate which is at least ten times greater than the actual data transmission rate, and selects optimal digitized data samples prior to transmission.

6. The medical data transmission system of claim 5, wherein said pre-transmission processing means selects optimal digitized data samples prior to transmission by:
   (a) calculating the minimum, maximum and average values for a set of said digitized data samples;
   (b) if the difference between the minimum and maximum values is less than or equal to 15% of the full scale range of said analog-to-digital converter, selecting and transmitting the average value for said set of digitized data sample;
   (c) if the difference between the minimum and maximum values is greater than 15% of the full scale range of said analog-to-digital converter, and the average value for said set of digitized data samples is less than the average value for the preceding set of data samples, selecting and transmitting the minimum value for said set of digitized data samples; and
   (d) if the difference between the minimum and maximum values is greater than 15% of the full scale range of said analog-to-digital converter, and the average value for said set of digitized data samples is greater than the average value for the preceding set of data samples, selecting and transmitting the maximum value for said set of digitized data samples.

7. The medical data transmission system of claim 1, wherein said data transmission linkage comprises a transmitting computer coupled with a receiving computer over a transmission medium via a pair of modems.

8. The medical data transmission system of claim 7, wherein said transmission medium comprises a voice-grade telephone line.

9. The medical data transmission system of claim 1, wherein said post-transmission processing means buffers said digitized data upon receipt to ensure continuous analog signal reconstruction.

10. The medical data transmission system of claim 1, wherein said post-transmission processing means performs a smoothing method on said digitized data.

11. The medical data transmission system of claim 10, wherein said smoothing method comprises the insertion of intervening data points into said digitized data.

12. The medical data transmission system of claim 1, wherein said post-transmission processing means further comprises a digital-to-analog converter for reconstructing said detected analog signal corresponding to said physiological parameter of said patient.

13. A method for the transmission of medical data through a transmission medium, comprising:
   (a) detecting at least one physiological parameter from a patient;
   (b) pre-processing the analog signals corresponding to said detected physiological parameter into digitized data samples;
   (c) simultaneously transmitting said digitized data samples across more than ten transmission channels to a receiving location in real-time; and
   (d) post-processing said digitized data samples at said receiving location prior to analyzing said physiological parameter from said patient.

14. The medical data transmission method of claim 13, wherein said physiological parameter is selected from the group comprising: EEG signals, EKG signals, EMG signals, EOG signals, respiration signals, and oximetry signals.

15. The medical data transmission method of claim 13, wherein said pre-processing step further comprises digitally sampling said analog signals at a rate which is at least ten times greater than the actual data transmission rate, and performing a data reduction method on the digitized data samples.

16. The medical data transmission method of claim 15, wherein said data reduction method further comprises:

(a) calculating the minimum, maximum and average values for a set of said digitized data samples;

(b) if the difference between the minimum and maximum values is less than 15% of the full scale range of the analog-to-digital converter, selecting and transmitting the average value for said set of digitized data samples;

(c) if the difference between the minimum and maximum values is greater than 15% of the full scale range of the analog-to-digital converter, and the average value for said set of digitized data samples is less than the average value for the preceding set of data samples, selecting and transmitting the minimum value for said set of digitized data samples; and (d) if the difference between the minimum and maximum values is greater than 15% of the full scale range of the analog-to-digital converter, and the average value for said set of digitized data samples is greater than the average value for the preceding set of data samples, selecting and transmitting the maximum value for said set of digitized data samples.

17. The medical data transmission method of claim 13, wherein said post-processing step further comprises performing a smoothing method on said digitized data samples.

18. The medical data transmission method of claim 17, wherein said smoothing method comprises the insertion of intervening data points into said digitized data.

19. The medical data transmission method of claim 17, wherein said post-processing step further comprises buffering said digitized data for a predetermined length of time prior to performing said smoothing method on said digitized data samples.

20. A medical data transmission system, comprising:

(a) a detection means for detecting at least one physiological parameter from a patient;

(b) a pre-transmission processing means for digitally sampling the detected analog signals and selecting optimal digitized data samples for transmission, said pre-transmission processing means coupled to said detection means;

(c) a data transmission linkage comprising a transmitting computer coupled with a receiving computer over a telephone line via two modems, which transmits more than ten channels of said digitized data samples to a receiving location, said data transmission linkage coupled to said pre-transmission processing means;

(d) a post-transmission processing means coupled to said data transmission linkage at said receiving location for buffering said digitized data samples and performing a smoothing method on said digitized data samples prior to analyzing said physiological parameter from said patient.

* * * * *